United States Patent
Lean et al.

(10) Patent No.: US 7,282,129 B2
(45) Date of Patent: Oct. 16, 2007

(54) TRAVELING WAVE ALGORITHMS TO FOCUS AND CONCENTRATE PROTEINS IN GEL ELECTROPHORESIS

(75) Inventors: Meng H. Lean, Santa Clara, CA (US); Huangpin Ben Hsieh, Mountain View, CA (US); John S. Fitch, Los Altos, CA (US); Armin R. Völkel, Mountain View, CA (US); Bryan Preas, Palo Alto, CA (US); Scott Elrod, La Honda, CA (US); Richard H. Bruce, Los Altos, CA (US); Eric Peeters, Fremont, CA (US); Frank Torres, San Jose, CA (US); Michael Chabinyc, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 746 days.

(21) Appl. No.: 10/460,137

(22) Filed: Jun. 12, 2003

(65) Prior Publication Data

US 2004/0251139 A1 Dec. 16, 2004

(51) Int. Cl.
*G01N 27/447* (2006.01)
(52) U.S. Cl. ..................... 204/547; 204/458
(58) Field of Classification Search .............. 204/643, 204/547, 609, 458
See application file for complete search history.

(56) References Cited

U.S. PATENT DOCUMENTS

| 4,473,452 | A | 9/1984 | Cantor et al. |
|---|---|---|---|
| 4,647,179 | A | 3/1987 | Schmidlin |
| 4,737,251 | A | 4/1988 | Carle et al. |
| 5,208,458 | A | 5/1993 | Busch et al. |
| 5,534,121 | A | 7/1996 | Merrick et al. |
| 5,569,364 | A * | 10/1996 | Hooper et al. .............. 204/455 |
| 5,645,702 | A * | 7/1997 | Witt et al. .................. 204/501 |
| 5,653,859 | A | 8/1997 | Parton et al. |
| 5,837,116 | A | 11/1998 | Harrington et al. |
| 6,272,296 | B1 | 8/2001 | Gartstein |
| 6,296,752 | B1 | 10/2001 | McBride et al. |
| 6,358,752 | B1 | 3/2002 | Durst et al. |
| 6,398,933 | B1 | 6/2002 | Scott |
| 6,499,831 | B2 | 12/2002 | Schmidlin |

(Continued)

FOREIGN PATENT DOCUMENTS

WO   WO 00/73780   12/2000

(Continued)

OTHER PUBLICATIONS

Morishima et al. ( << Novel separation method in a Chip using Capillary Electrophoresis in Combination with Dielectrophoresis, >> Micro Total Analysis Systems 2000. 269-272).*

(Continued)

*Primary Examiner*—Alex Noguerola
(74) *Attorney, Agent, or Firm*—Fay Sharpe LLP

(57) ABSTRACT

An electrophoretic cell configuration and related method are disclosed that employ oppositely directed traveling electrical waves. The waves travel across the cell and samples undergoing separation. Various strategies are used to selectively direct the movement and arrangement of the samples and resulting sample patterns.

11 Claims, 4 Drawing Sheets

U.S. PATENT DOCUMENTS

2001/0023825 A1     9/2001     Frumin et al.
2002/0144895 A1    10/2002     Stern et al.

FOREIGN PATENT DOCUMENTS

WO        WO 01/05514 A1 *    1/2001

OTHER PUBLICATIONS

Hagedorn R et al: "Traveling-Wave Dielectrophoresis of Microparticles," Electrophoresis, Weinheim, DE, vol. 13, No. 1/2, Jan. 1992, pp. 49-54.

Dunphyet al., *Rapid Separation and Manipulation of DNA by a Ratcheting Electrophoresis Microchip (REM)*, Nov. 17-22, 2002, pp. 419-423, ASME, USA.

Proteome Systems, Products, Website, *ElectrophoretIQ³*, 2002 at http://www.proteomesystems.com/product/product.asp-?ProductID=43 and http://www.proteomesystems.com/product/profile.asp?DocumentID=662.

ISC Buyers' Guide, Website, *Electrophoresis, 2D Gel*, 2002, at http://www.iscpubs.com/bg/us/prod/prod1991.html.

EMBL's Proteomics Visitor Facility, Website, 2D Gel Equipment, *Protean 2D Cells from Bio-Rad*, 2001, at http://.mann.embl-heidelberg.de/Visitor_Facility/PageLinks/Instrumentation/GelchamberMain.html, and *Protean IEF Cell from Bio-Rad*, at http://www.mann.embl-heidelberg.de/Visitor_Facility/PageLinks/Instrumentation/ECellMain.html.

James R. Jefferies,, *2D Gel Electrophoresis for Proteomics Tutorial*, pp. 1-24 at http://www.aber.ac.uk/parasitology/Proteome/Tut_2D.html (last tutorial update: Jan. 7, 2003).

The Scripps Research Institute, Website, *Proteomics Module*, 2003, pp. 1-3 at http://core-eye.scripps.edu/proteomics.htm.

2D Protocols, Website, *Analysis of Proteins Using Small Format 2D Gel Electrophoresis*, 2000, pp. 1-5, at http://www.abdn.ac.uk/~mmb0236/protocol.htm.

Biowire.com, Website, *The Nucleus*, 2000-2002, pp. 1-4 at http://www.biowire.com/nucleus/nucleus_1_3.jsp.

Bio-Rad Laboratories, Website, *Electrophoresis*, 2003, at http:www.bio-rad.com/B2B/BioRad/produict/br_category.jsp.

Scott Rudge et al., Electroseparations (Electrophoresis), *Encyclopedia of Chemical Technology*, 4th Edition, vol. 9, pp. 356-376, publication date is unavailable.

O'Hara et al., *Ratcheting Electrophoresis Microschip (REM) for Programmable Transport and Separation of Macromolecules*, MEMS, Nov. 11-16, 2001, pp. 619-628, vol. 3, ASME, USA.

* cited by examiner

TRAVELING WAVE ALGORITHMS TO FOCUS AND CONCENTRATE PROTEINS IN GEL ELECTROPHORESIS

TECHNICAL FIELD

The present invention relates to the field of electrophoretic separation of molecules, and, more particularly, to their focusing into narrow bands in gel electrophoresis. The present invention also relates to analytical methods based upon the observation of the migration of particles in response to an electric field.

BACKGROUND OF THE INVENTION

Electrophoresis is a separation technique most often applied to the analysis of biological or other polymeric samples. It has frequent application to analysis of proteins and DNA fragment mixtures. The high resolution of electrophoresis has made it a key tool in the advancement of biotechnology. Variations of this methodology are used for DNA sequencing, isolating active biological factors associated with diseases such as cystic fibrosis, sickle-cell anemia, myelomas, and leukemia, and establishing immunological reactions between samples on the basis of individual compounds. Electrophoresis is an extremely effective analytical tool because it does not affect a molecule's structure, and it is highly sensitive to small differences in molecular charge and mass.

Electrophoresis in a polymeric gel, such as a polyacrylamide gel or an agarose gel, adds two advantages to an electrophoretic system. First, the polymeric gel stabilizes the electrophoretic system against convective disturbances. Second, the polymeric gel provides a porous passageway through which the molecules must travel. Since larger molecules will travel more slowly through the passageways than smaller molecules, use of a polymeric gel permits the separation of molecules by molecular size.

One common electrophoretic procedure is to establish solutions having different pH values at each end of an electric field, with a gradient range of pH in between. At a certain pH, the isoelectric point of a molecule is obtained and the molecule carries no net charge. As the molecule crosses the pH gradient, it reaches an isoelectric point and is thereafter immobile in the electric field. Therefore, this electrophoresis procedure separates molecules according to their different isoelectric points.

More specifically, this procedure is referred to as isoelectric focusing (IEF) in which an electric field is applied to a molecule in a pH gradient to mobilize the molecule to a position in the pH gradient at which its net charge is zero, i.e., the isoelectric point of the molecule. It often is used to separate proteins in a mixture and as an aid in the characterization of biomolecules of unknown composition. Commercially available gradients may be utilized in isoelectric focusing which consist of multicharged ampholytes, with closely spaced isoelectric values and high conductivity, which partition into a pH gradient upon application of an electric field. The ampholytes are generally provided in a support matrix, such as a polyacrylamide gel.

Because protein samples are actually ampholytes, when samples are loaded onto the gel and a current is applied, the compounds migrate through the gel until they come to their isoelectric point where they reach a steady state. Isoelectric focusing takes a long time (from about 3 to 30 hours) to complete because sample compounds move more and more slowly as they approach the pH in the gel that corresponds to their isoelectric points. Because the gradient ampholytes and the samples stop where they have no mobility, the resistivity of the system increases dramatically toward the end of the experiment, and the current decreases dramatically. For this reason, isoelectric focusing is usually run with constant voltage. Constant current application can lead to overheating of the system.

The combination of sodium dodecyl sulfate (SDS), $CH_3(CH_2)_{10}CH_2OSO_3Na$, also known as lauryl sulfate, treatment of samples and polyacrylamide gel electrophoresis was first described in the late 1960s. SDS is an ionic surfactant which solubilizes and denatures proteins. The surfactant coats a protein through hydrophobic interactions with the polypeptide backbone, effectively separating most proteins into their polypeptide subunits. The majority of proteins to which SDS binds then unfold into linear molecules having a similar surface potential.

SDS-polyacrylamide gel electrophoresis (SDS-PAGE) allows separation of molecules strictly on the basis of size, i.e., molecular weight. When SDS-treated samples migrate into a gel and are electrophoresed, the principal difference is size or length. Smaller molecules travel through the matrix more quickly than those that are larger. The rate at which molecules migrate through a polyacrylamide gel is inversely linear with the logarithm of their molecular weight. Thus denatured samples can be analyzed alongside standards of known molecular weight to aid in the interpretation of a substance's physical size.

Two-dimensional (2D) electrophoresis is unique, offering an analytical method that is both reproducible and sensitive. It is referred to as 2D because it employs two different methods of electrophoresis, in two different dimensions, to produce one result. Each method separates the sample compounds based on different properties of each compound. The combination of the two methods gives better resolution of the compounds in the sample than could be achieved with either method alone. For example, each method alone may separate up to 100 components of a sample, whereas together they may separate up to 10,000 components.

A pair of electrophoretic techniques commonly employed in 2D analyses are the previously noted isoelectric focusing (IEF) and SDS-polyacrylamide gel electrophoresis (SDS-PAGE). IEF separates sample compounds according to isoelectric point, whereas SDS-PAGE separates the compounds by molecular weight. A 2D analytical technique using IEF and SDS-PAGE to separate proteins results in a gel having bands or spots in a random pattern. Each spot represents a unique component of a sample. A single charge difference in a component can be identified on the gel by a unique spot. This property of 2D electrophoresis, which allows identification of identical proteins that differ by one charge difference, has made it an invaluable technique for the molecular genetic community.

As noted, many proteins are separated by polyacrylamide gel electrophoresis (PAGE) (based on the molecular weight) or modified polyacrylamide gel isoelectric focusing (IEF) (based on molecular charge). Both of the techniques can be used in tandem in a two-dimensional approach for maximum resolution. Polyacrylamide gels are made by polymerizing the monomer, acrylamide, into long strands, and then linking the strands together with a cross-linker, usually N,N'-methylene-bis-acrylamide (bis). The relative proportions of these components will determine the separation characteristics of the gel. Isoelectric focusing is carried out in a PAGE gel that contains an immobilized pH gradient consisting of high molecular weight polyaminocarboxylic acid (ampholytes). The separation power of two dimensional polyacrylamide gel electrophoresis (2D PAGE) has often been exploited as part of isolation schemes for determining the amino acid sequence of unknown proteins from complex protein mixtures.

Particles can be manipulated by subjecting them to traveling electric fields. Such traveling fields are produced by applying appropriate voltages to microelectrode arrays of suitable design. Traveling electric fields are generated by applying voltages of suitable frequency and phases to the electrodes.

This technique of using traveling electric fields relates to an important method for separation and sorting of large particles and cells referred to as dielectrophoresis. Dielectrophoresis is defined as the movement of a polarisable particle in a non-uniform electric field. Essentially, the force arises from the interaction of the field non-uniformity with a field induced charge redistribution in the separated particle.

Particles are manipulated using non uniform electric fields generated by various configurations of electrodes and electrode arrays. As a general biotechnological tool, dielectrophoresis is extremely powerful. From a measurement of the rate of movement of a particle the dielectric properties of the particle can be determined. More significantly, particles can be manipulated and positioned at will without physical contact, leading to new methods for separation technology.

A powerful extension of dielectrophoresis separation is traveling wave dielectrophoresis (TWD) in which variable electric fields are generated in a system of electrodes by applying time varying electric potential to consecutive electrodes. Such a method of Traveling Wave Field Migration was described by Parton et al. in U.S. Pat. No. 5,653,859, herein incorporated by reference. Although satisfactory, this work is not directed to the field of protein analyses and in particular, to 2D gel electrophoresis techniques.

A microfluidic device for electrophoretic separation of biomolecules such as DNA and protein was described by Dunphy et al. in "Rapid Separation and Manipulation of DNA by a Ratcheting Electrophoresis Microchip (REM)," Proceedings of IMECE2002, Nov. 17-22, 2002, New Orleans, La., No. IMECE2002-33564, herein incorporated by reference. The device utilizes thousands of electrodes along the length of a microchannel. An electrical potential is applied across the electrodes and selectively varied to separate molecules within the microchannel into two groups using a ratcheting mechanism. This mechanism does not employ traveling waves. Although directed to the separation of biomolecules, this strategy is based upon micro device technology and is not readily compatible with conventional laboratory proteomic equipment. Moreover, the strategy described by Dunphy et al. is silent with regard to applications involving 2D gel electrophoretic techniques. Accordingly, a need exists for a device and technique for utilizing electrostatic traveling waves in conjunction with 2D gel electrophoresis techniques and equipment.

Two-dimensional gel electrophoresis is the acknowledged workhorse for proteomic research because it is simple, has high capacity, and is able to identify all proteins resolved on the gel when coupled with a mass spectrometer. However, lengthy process time, difficulty in resolving low-abundance proteins, and poor reproducibility, among other factors, has limited its full potential to becoming the definitive tool for proteomics. The present invention addresses many of these issues with a new instrument design and technique to reduce processing time and increase analytical resolution by reducing band broadening with electrostatic traveling waves (TW).

BRIEF DESCRIPTION OF THE INVENTION

A particular concern in the scientific community is the band broadening of proteins after SDS-PAGE. The cause is being debated in the literature, but includes contributions from diffusion, Coulomb repulsion, and gel matrix interaction. The present invention is complimentary in providing secondary processing capability to tighten, or focus, the protein band after the initial SDS-PAGE run. The strategy of the present invention is to use electrophoretic forces arising from electrostatic traveling waves from both sides of the protein distribution to move proteins inward, thus compacting them into a tighter patch. These waves require low voltage (0.5V to 1V) and relatively short processing times because of the high local electrical fields.

In a first aspect, the present invention provides a gel electrophoretic system comprising an electrophoretic cell including (i) a gel medium and, (ii) an electrical grid having a first end and a second end and a plurality of closely spaced parallel electrodes extending between the first and second ends and in electrical communication therewith. The system also comprises a voltage controller adapted to provide a multi-phase electrical signal at a first output end and at a second output of the controller. The first output is in electrical communication with the first end of the grid. The second output is in electrical communication with the second end of the grid. Upon operation of the controller a first traveling wave is generated at the first end of the grid which travels toward the second end of the grid. Additionally, a second traveling wave is generated at the second end of the grid which travels toward the first end of the grid. The first traveling wave and the second traveling wave intersect along the electrical grid generally between the first end and the second end. Typically this produces a standing wave which influences the migration of proteins or biomolecules disposed in the electrophoretic cell.

In another aspect, the present invention provides a method for compacting a biomolecule band or patch having undergone electrophoresis in a gel electrophoretic system. The system typically includes an electrophoretic cell with a gel medium, a band or patch of biomolecules in the gel, and an electrical grid. The grid has a plurality of closely spaced parallel electrodes extending between two sides of the grid. The system also includes a voltage controller adapted to provide a first multi-phase electrical signal at a first output in communication with one of the sides of the grid, and a second multi-phase electrical signal at a second output in communication with another side of the grid. The method comprises a step of generating the first multi-phase electrical signal at the first side of the grid. The method also comprises a step of generating a second multi-phase electrical signal at the other side of the grid. The signals travel toward one another and cause compaction of the band or patch of biomolecules in the gel.

In yet another aspect, the present invention provides a method for compacting a protein patch dispersed in a gel after electrophoretic separation. The method comprises a step of providing an electrode grid in close proximity to the gel and the protein patch dispersed therein. The grid has a plurality of closely spaced parallel electrodes. The method also comprises a step of providing a voltage controller adapted to provide a multi-phase electrical signal. The method additionally includes a step of applying the multi-phase electrical signal to (i) a first region of the electrode grid to thereby cause a first set of traveling electrostatic waves to travel from the first region toward a second region of the grid. The applying step also includes applying the multi-phase electrical signal to a second region of the electrode to thereby cause a second set of traveling electrostatic waves to travel from the second region toward the first region of the grid and in a direction opposite from the first set of traveling waves. The first set of traveling waves cause migration of at least a portion of the proteins toward the second region of the grid. The second set of traveling waves cause migration of at least another portion of the proteins toward the first region of the grid. This thereby compacts the patch.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1A:
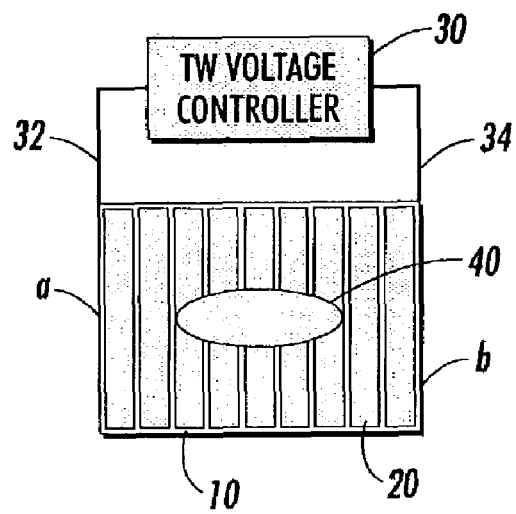
FIG. 1A is a schematic diagram of a preferred embodiment electrophoretic cell having an electrical grid and a traveling wave controller in accordance with the present invention.

Separation and identification of biomolecules such as proteins and DNA is an important step in biotechnology. In this post-genomic period, 2D gel electrophoresis is emerging as the workhorse for protein separation. The methodology is 30 years old and has seen mostly minor technology improvements. The present invention provides an apparatus and related method to improve resolution by compacting the protein patch using bidirectional traveling waves after the initial gel electrophoresis separation.

The primary objective of using electrostatic traveling waves is the very rapid transport of proteins or molecular components undergoing analysis that may be achieved by creating very high local electrical fields with low voltages using an electrode grid with a very fine pitch. The present invention provides several advantages over conventional gel setups including lower voltage (1V compared to 200V for PAGE and 8000V for IEF), and much higher transport velocities (up to 10 times or more). However, band broadening tends to occur due to the characteristic trait of this mode of transport. The present invention method provides the following strategy. First, the proteins are loaded such that they are within reach of the electrical fields from the traveling wave grid. Then, a series of traveling waves are generated for a period of time sufficient for the resulting motion of the proteins to be synchronized with the sweep frequency of the traveling wave signal. Once synchronized, the propagation velocity of the proteins in the operating regime of interest is approximately a linear function of the sweep frequency. Unless all proteins are completely loaded at any given time, the remnants contribute to band broadening as they are transported in succeeding traveling wave cycles.

The present invention is directed to compacting a protein patch or other groups of biomolecules using traveling wave excitation. The patch may be the result of conventional gel electrophoresis or 2D PAGE or from an initial fast traveling wave separation. An initial separation process may be used to rapidly separate out the major proteins onto designated regions of the traveling wave grid based on sweep frequency. Details of various preferred assemblies, systems, and methods are as follows.

A preferred embodiment gel electrophoretic system in accordance with the present invention includes an electrophoretic cell and a voltage controller. The cell includes an effective amount of an electrophoretic gel in intimate relation with an electrode grid. The grid generally includes a collection of electrodes that extend in a parallel fashion across the cell. The voltage controller is configured or otherwise set to provide a multi-phase electrical signal across two opposite ends of the grid. That is, a first multi-phase signal is applied at one end of the grid and a second multi-phase signal is applied at the other, opposite end of the grid. As described herein, it is most preferred that individual phases of the two signals are simultaneously applied at opposite ends of a common electrode. Generation or application of the multi-phase signals at opposite ends of the grid results in electrostatic waves that travel across the grid. One set of waves travel in one direction across the grid and another set of waves travel in an opposite direction across the grid. Depending upon the timing and configuration of signal phases to electrodes of the grid, the intersection of the waves can be selectively tailored to occur at particular regions of the grid, and in specific fashions to selectively migrate or direction biomolecules residing within the gel.

More specifically, FIG. 1A is a schematic diagram of a preferred embodiment electrophoretic cell 10 having an electrical grid 20 disposed along one or both faces of the cell. The cell includes a gel medium and an electrical grid 20 in intimate relation with the medium. The electrical grid 20 preferably includes a first end and a second end with a collection of closely spaced parallel electrodes. The electrodes extend between the first end and the second end of the grid. It is preferred that the electrodes extend in a direction that is generally transverse to the primary direction or axis of travel of the proteins or biomolecules traveling through the gel. FIG. 1A also illustrates a traveling wave voltage controller 30 in electrical communication with the grid 20. The voltage controller is configured to provide a multi-phase electrical signal at a first output 32 and a multi-phase electrical signal at a second output 34. Region 40 represents a protein patch or other collection of biomolecules or components that have undergone band broadening or other undesirable propagation across the cell 10.

Figure 1B:
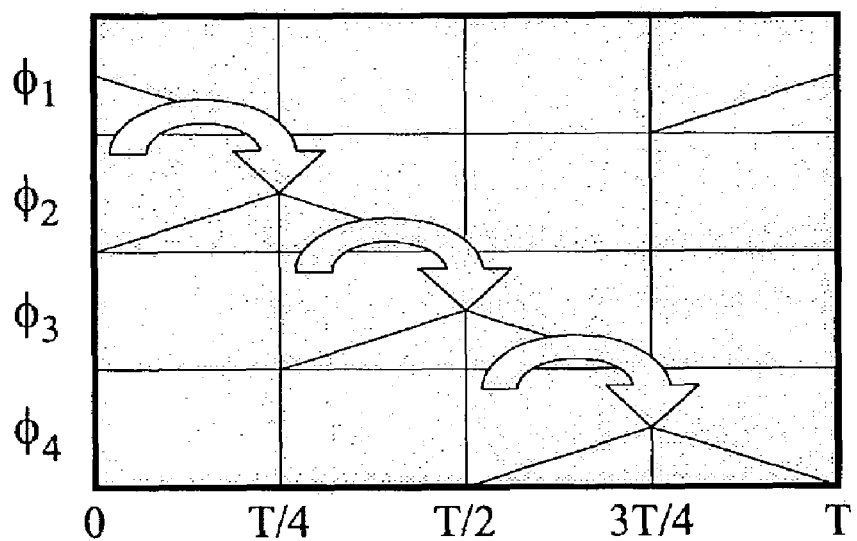
FIG. 1B is a preferred wave diagram illustrating a voltage pattern applied to a first side of the grid of the cell shown in FIG. 1A.
Figure 1C:
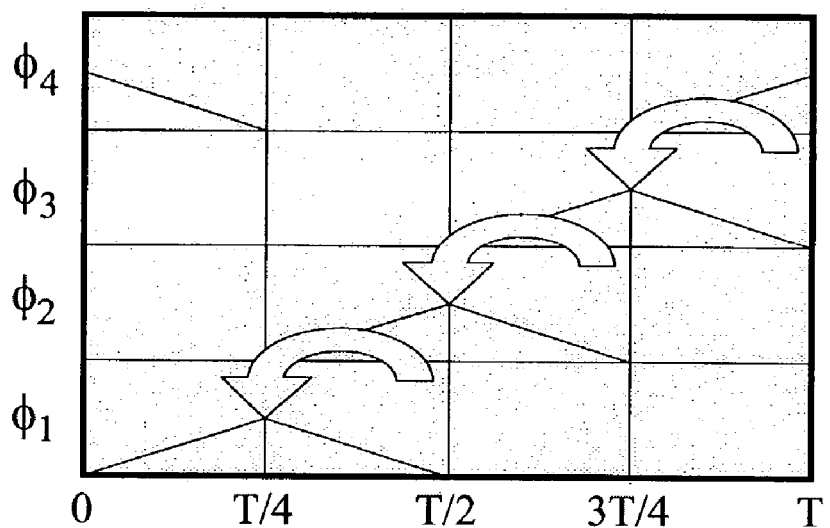
FIG. 1C is a preferred wave diagram illustrating a voltage pattern applied to a second side, opposite from the first side, of the grid of the cell shown in FIG. 1A.
Figure 1D:
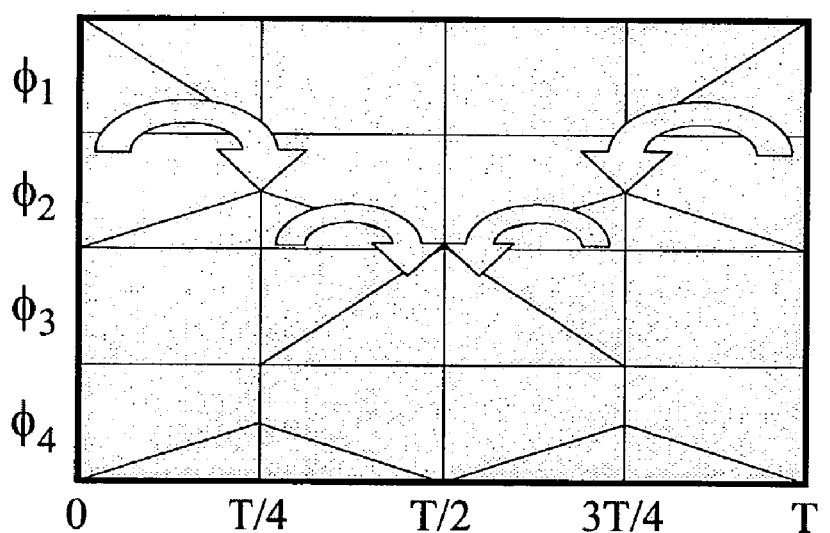
FIG. 1D is a preferred wave diagram illustrating a voltage pattern resulting from the addition of the two voltage patterns of FIGS. 1B and 1C.

Two traveling waves are generated across the cell 10 and through the grid 20, one from each side, such as sides a and b. Since the basis for motion of the biomolecules, or components thereof, is the traveling wave, in one preferred embodiment, two simultaneous and oppositely directly traveling waves are generated which produce a standing wave of the desired waveform. This is illustrated in FIGS. 1B to 1D where the two wave diagrams, each one depicting a voltage pattern applied on a corresponding side of the grid 20, show the voltage patterns over a four (4) phase cycle. Specifically, FIG. 1B illustrates an electrical signal applied to side a of the cell 10 in FIG. 1A. The four phase voltage signal varies as a function of time, as shown on the axis designed "T." Preferably, each phase is applied to a corresponding electrode of the grid 20. More specifically, each phase is applied to an electrical contact pad which in turn is in electrical communication with a corresponding electrode of the grid 20. FIG. 1C illustrates another electrical signal applied to side b of the cell 10 in FIG. 1A. The four phase voltage signal varies as a function of time as previously described with respect to FIG. 1B. Preferably, each phase is applied to a corresponding electrode or contact pad of the grid 20. The contact pads along side a of the cell 10 are in electrical communication with the contact pads along side b of the cell 10 through corresponding electrodes. The electrical signal applied at side a travels toward side b, and the electrical signal applied at side b travels toward side a. The correspondence between the contact pads and phases of the electrical signal(s) applied along sides a and b is as follows:

TABLE 1

Contact Pad Mapping

| Contact Pads Along Side a | Contact Pads Along Side b |
|---|---|
| $\phi_1$ | $\phi_4$ |
| $\phi_2$ | $\phi_3$ |
| $\phi_3$ | $\phi_2$ |
| $\phi_4$ | $\phi_1$ |

The addition of these two wave signals results in the voltage diagram shown in FIG. 1D. This standing wave of FIG. 1D results in a central sieving action with a directionality inclined towards the interior of the protein patch 40. Due to constructive interference, the voltage may sum on the center electrode or center region of the grid 20. Therefore, some consideration must be paid to ensure that this voltage value does not result in unduly high gas generation.

Figure 2A:
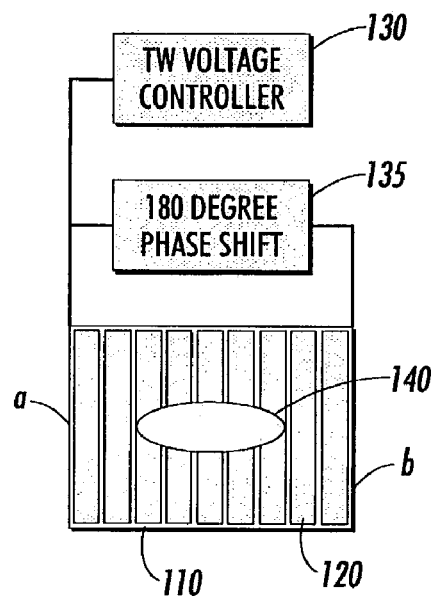
FIG. 2A is a schematic diagram of another preferred embodiment electrophoretic cell having an electrical grid and a traveling wave controller in accordance with the present invention.

Another strategy is to use two wave signals that are 180 degrees out of phase with respect to each other. Specifically, FIG. 2A is a schematic diagram of another preferred embodiment electrophoretic cell 110 having an electrical grid 120 disposed along one or both faces of the cell. FIG. 2A also illustrates a traveling wave voltage controller 130 and a phase shift component 135 in electrical communication with the controller 130 and the grid 120. Region 140 represents a protein patch or other array of biomolecules or components thereof that have undergone band broadening or other undesirable propagation across the traveling wave grid 120.

Figure 2B:
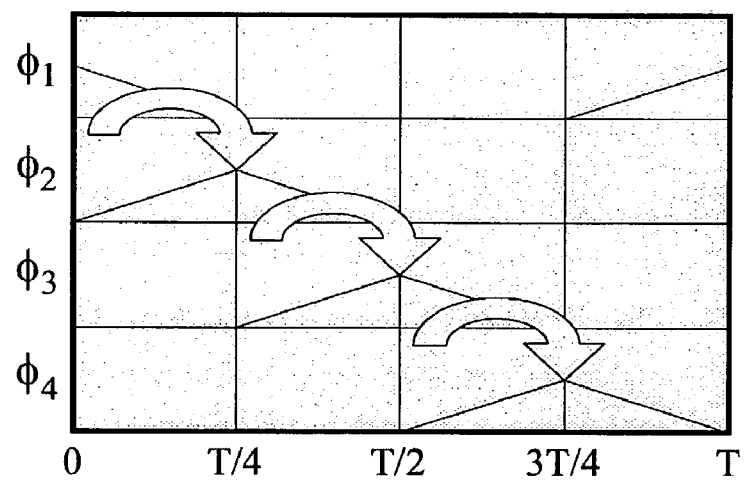
FIG. 2B is a preferred wave diagram illustrating a voltage pattern applied to a first side of the grid of the cell shown in FIG. 2A.
Figure 2C:
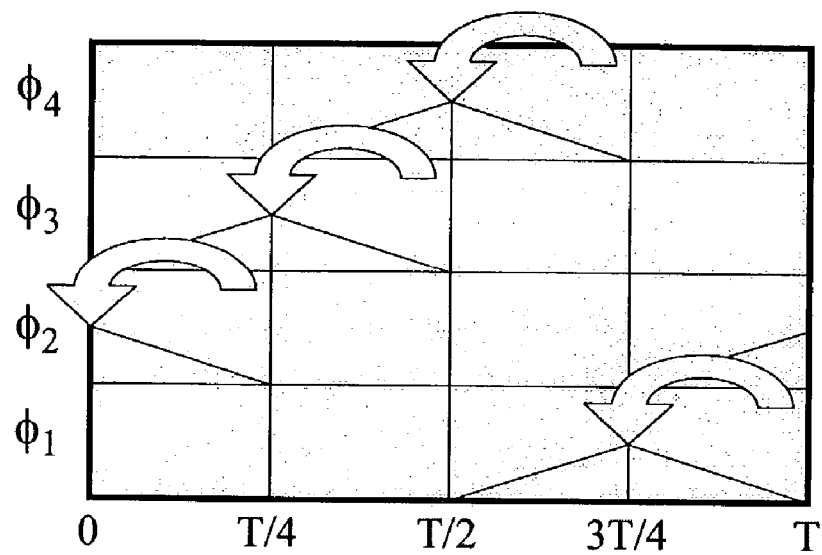
FIG. 2C is a preferred wave diagram illustrating a voltage pattern applied to a second side, opposite from the first side, of the grid of the cell shown in FIG. 2A.
Figure 2D:
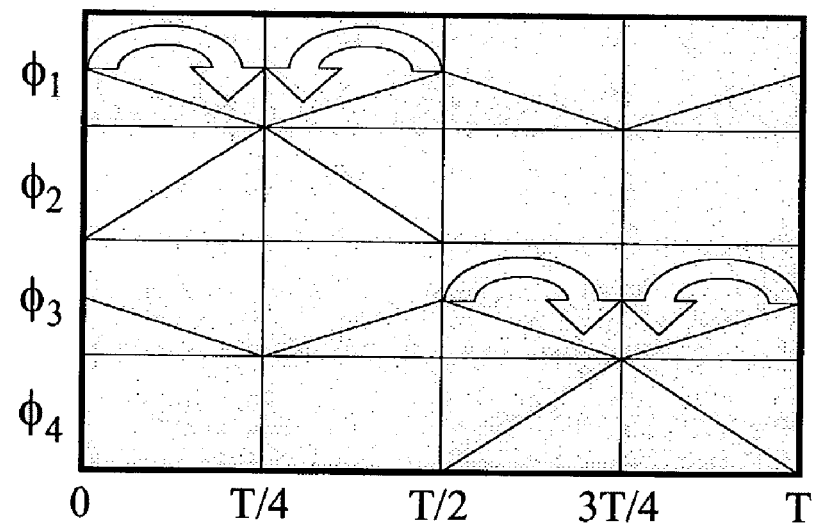
FIG. 2D is a preferred wave diagram illustrating a voltage pattern resulting from the addition of the two voltage patterns of FIGS. 2B and 2C.

In accordance with a preferred technique of the present invention, two traveling waves are generated across the grid, one from each side such as sides a and b. That is, two simultaneous and oppositely directed traveling waves are generated which produce a standing wave of the desired waveform. This is illustrated in FIGS. 2B to 2D where the two wave diagrams, each applied to an opposite side of the grid 120, show the voltage patterns over the 4-phase cycle. Preferably, the cell 110 includes a pair of corresponding contact pads that are in electrical communication with each other through a plurality of electrodes extending across the cell 110. The correspondence between the contact pads and phases of the electrical signal(s) applied along sides a and b of the cell 110 is as follows:

TABLE 2

Contact Pad Mapping

| Contact Pads Along Side a | Contact Pads Along Side b |
|---|---|
| $\phi_1$ | $\phi_2$ |
| $\phi_2$ | $\phi_1$ |
| $\phi_3$ | $\phi_4$ |
| $\phi_4$ | $\phi_3$ |

The addition of these two wave signals results in the voltage diagram shown in FIG. 2D. This standing wave of FIG. 2D results in a zigzag motion with a directionality inclined towards the interior of the patch.

A wide array of commercially available electrophoretic equipment may be modified or retrofitted in accordance with the present invention. Gel electrophoretic systems and cells, immobilized pH gradient (IPG) strips, power sources, and controllers therefore may be obtained from one or more of the following suppliers: Proteome Systems Limited; Bio-Rad Laboratories; AMRESCO, Inc.; Invitrogen Corp.; Owl Separations Systems; R. Shadel Inc.; Stratagene; Zaxis, Inc.; and Amersham Biosciences.

Electrical grids may be formed on one or both sides of a cell. Preferably, the grid is an array of parallel electrodes, each having a relatively fine width and constant spacing from adjacent electrodes. The electrodes are connected to a voltage controller which is preferably a programmable controller. The voltage biases are applied to the electrodes, and specifically as described in conjunction with the preferred embodiments herein.

The present invention systems and methods can be employed in a variety of fashions. The systems and methods are particularly beneficial for secondary processing of initially separated proteins or other biomolecules. Additionally, the present invention systems and methods are useful for compacting bands or patches of proteins after transfer from an IPG strip to a 2D gel, and prior to SDS-PAGE. This is performed in the stacking layer to tighten the band prior to actual separation.

Although a wide array of configurations, arrangements, and dimensions may be used for the electrodes and electrode grids described herein, several representative aspects are as follows. The electrode pitch preferably is in the range of from about 600 μm to about 10 μm, and more preferably from about 200 μm to about 40 μm. The spacing between opposing edges of adjacent electrodes is preferably from about 300 μm to about 7.5 μm and more preferably from about 100 μm to about 30 μm. The preferred voltage level applied to the grid and electrodes is from about 5 V to about 0.001 V, and more preferably about 2V to about 0.10 V. The preferred frequency of the electrical signal depends upon the biomolecules to be migrated, however, frequencies in the range of from about 0.001 to about 10 Hz have been found useful, with preferred frequencies being from about 2 to about 0.020 Hz.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method for compacting a biomolecule band or patch having undergone electrophoresis in a gel electrophoretic system including (i) an electrophoretic cell with a gel medium, a band or patch of biomolecules in said gel, and an electrical grid, said grid having a plurality of closely spaced parallel electrodes extending between a first side of said grid and a second side of said grid, and (ii) a voltage controller adapted to provide a first multi-phase electrical signal at a first output in communication with said first side of said grid and a second multi-phase electrical signal at a second output in communication with said second side of said grid, said method comprising:
    electrophoretically separating a biomolecule sample to thereby produce a band or patch of biomolecules in said gel;
    generating said first multi-phase electrical signal at said first side of said grid;
    generating said second multi-phase electrical signal at said second side of said grid;
    thereby causing compaction of said band or patch of biomolecules in said gel.

2. The method of claim 1 wherein said step of generating said second multi-phase electrical signal occurs concurrently with said step of generating said first multi-phase electrical signal.

3. he method of claim 1 wherein said step of generating said first multi-phase electrical signal causes a first traveling wave to migrate from said first side of said grid toward said second side of said grid, and said step of generating said second multi-phase electrical signal causes a second traveling wave to migrate from said second side of said grid toward said first side of said grid, thereby resulting in compacting of said band or patch of biomolecules within said gel.

4. A method for compacting a protein patch dispersed in a gel after electrophoretic separation, said method comprising:
    electrophoretically separating a protein sample to thereby produce a protein patch in said gel;
    providing an electrode grid in close proximity to said gel and said protein patch dispersed therein, said grid having a plurality of closely spaced parallel electrodes;
    providing a voltage controller adapted to provide a multi-phase electrical signal;
    applying said multi-phase electrical signal to (i) a first region of said electrode grid to thereby cause a first set of traveling electrostatic waves to travel from said first region toward a second region of said grid, and (ii) said second region of said electrode grid to thereby cause a second set of traveling electrostatic waves to travel from said second region toward said first region of said grid, and in a direction opposite from said first set of traveling waves;
    whereby said first set of traveling waves cause migration of at least a portion of said proteins toward said second region of said grid and said second set of traveling waves cause migration of at least another portion of said proteins toward said first region of said grid, thereby compacting said patch.

5. The method of claim 4 wherein said multi-phase electrical signal is a four (4) phase signal.

6. The method of claim 5 wherein said applying step is performed by:
    applying a first phase of said signal to a first end of an electrode and applying a fourth phase of said signal to a second end, opposite from said first end, of said electrode.

7. The method of claim 6 wherein said applying step is performed by:
    applying a second phase of said signal to a first end of a second electrode and applying a third phase of said signal to a second end of said second electrode.

8. The method of claim 7 wherein said applying step is performed by:
    applying a third phase of said signal to a first end of a third electrode and applying a second phase of said signal to a second end of said third electrode.

9. The method of claim 5 wherein said electrical signal provided by said voltage controller is a first electrical signal, said method further comprising:
    providing a phase shift component in electrical communication with said controller to thereby provide a second electrical signal that is out of phase from said first electrical signal;
    applying a first phase of said first signal to a first end of a first electrode and applying a second phase of said second signal to a second end of said first electrode, said second end opposite from said first end.

10. The method of claim 9 further comprising:
    applying a second phase of said first signal to a first end of a second electrode and applying a first phase of said second signal to a second end of said second electrode.

11. The method of claim 10 further comprising:
    applying a third phase of said first signal to a first end of a third electrode and applying a fourth phase of said second signal to a second end of said third electrode.

* * * * *